(12) United States Patent
Noll (10) Patent No.: US 7,745,208 B2
(45) Date of Patent: Jun. 29, 2010

(54) ANGLED REACTION VESSEL

(76) Inventor: Anthony P. Noll, 4641 Augusta Minerva Rd., Augusta, KY (US) 41002-8927

( * ) Notice: Subject to any disclaimer, the term of this patent is extended or adjusted under 35 U.S.C. 154(b) by 947 days.

(21) Appl. No.: 11/355,632

(22) Filed: Feb. 15, 2006

(65) Prior Publication Data

US 2007/0190643 A1 Aug. 16, 2007

(51) Int. Cl.
*C12M 1/02* (2006.01)
*C12M 1/10* (2006.01)
*C12M 1/00* (2006.01)

(52) U.S. Cl. ............... 435/290.3; 435/289.1; 435/290.1; 435/290.2; 435/291.5; 435/298.1; 435/298.2; 435/291.7; 435/290.4; 71/9; 71/11; 71/12; 71/13; 71/14; 71/15; 366/330.1; 366/319

(58) Field of Classification Search ............... 435/290.3, 435/209.1, 290.2, 290.4, 291.5, 298.1, 289.1, 435/298.2, 291.7, 290.1; 71/9, 11, 12, 13, 71/14, 15; 366/319, 330.1
See application file for complete search history.

(56) References Cited

U.S. PATENT DOCUMENTS

| 742,226 | A | 10/1903 | Peck et al. |
|---|---|---|---|
| 2,317,992 | A | 5/1943 | Grether |
| 2,823,106 | A | 2/1958 | Pierson |
| 2,969,277 | A | 1/1961 | Carlsson et al. |
| 3,055,744 | A | 9/1962 | Peterson |
| 3,057,769 | A | 10/1962 | Sandberg |
| 3,070,156 | A | 12/1962 | Starrett |
| 3,235,369 | A | 2/1966 | Eweson |
| 3,236,604 | A | 2/1966 | Pierson |
| 3,524,594 | A | 8/1970 | Anderson et al. |
| 3,549,010 | A | 12/1970 | Marsh et al. |
| 3,549,092 | A | 12/1970 | Baxter, Jr. |
| 3,587,851 | A | 6/1971 | Anderson |

(Continued)

FOREIGN PATENT DOCUMENTS

EP 0277507 A2 1/1993

(Continued)

OTHER PUBLICATIONS

International Bureau, Notification Concerning Transmittal of International Preliminary Report on Patentability, Written Opinion of the International Searching Authority, International Preliminary Report, International Application No. PCT/US2007/061827, Aug. 28, 2008 date of mailing, 6 pages.

(Continued)

*Primary Examiner*—William H Beisner
*Assistant Examiner*—Nathan A Bowers
(74) *Attorney, Agent, or Firm*—Wood, Herron & Evans, LLP (57) ABSTRACT

The invention is an apparatus and a process for treating biomass bearing material including municipal solid waste (MSW). The apparatus includes a reaction vessel held at an angle and configured for rotation and steam injection, with helically arranged internal flights, a self-aligning door closure, and a swing-away door assembly. It also includes a novel structure for shredding biomass bearing material attached to the edges of the flights. This structure is a number of projecting tooth like points and paddles.

29 Claims, 8 Drawing Sheets

U.S. PATENT DOCUMENTS

| | | | |
|---|---|---|---|
| 3,595,488 A | 7/1971 | Blakley et al. | |
| 3,597,308 A | 8/1971 | Brooks | |
| 3,643,797 A | 2/1972 | Berkowitz et al. | |
| 3,668,286 A | 6/1972 | Brooks et al. | |
| 3,714,038 A | 1/1973 | Marsh | |
| 3,725,538 A | 4/1973 | Brewer | |
| 3,736,223 A | 5/1973 | Marsh | |
| 3,741,863 A | 6/1973 | Brooks | |
| 3,833,117 A | 9/1974 | Mackenzie et al. | |
| 3,849,246 A | 11/1974 | Raymond et al. | |
| 3,932,166 A | 1/1976 | Vignovich et al. | |
| 3,933,577 A | 1/1976 | Penque | |
| 3,939,286 A | 2/1976 | Jelks | |
| 3,961,913 A | 6/1976 | Brenneman et al. | |
| 3,993,577 A | 11/1976 | Black et al. | |
| RE29,156 E | 3/1977 | Marsh | |
| 4,010,098 A | 3/1977 | Fassell | |
| 4,033,907 A | 7/1977 | Wolf | |
| 4,044,695 A | 8/1977 | Mackenzie et al. | |
| 4,056,380 A | 11/1977 | Thiac | |
| 4,079,837 A | 3/1978 | Grube et al. | |
| 4,106,627 A | 8/1978 | Watanabe et al. | |
| 4,111,800 A | 9/1978 | Harendza-Harinxma | |
| 4,152,119 A | 5/1979 | Schulz | |
| 4,157,961 A | 6/1979 | Borst | |
| 4,185,680 A | 1/1980 | Lawson | |
| 4,225,457 A | 9/1980 | Schulz | |
| 4,235,707 A | 11/1980 | Burke, Jr. | |
| 4,264,352 A | 4/1981 | Houser | |
| 4,297,322 A | 10/1981 | Liu | |
| 4,312,701 A | 1/1982 | Campbell | |
| 4,321,150 A | 3/1982 | McMullen | |
| 4,342,830 A | 8/1982 | Holloway | |
| 4,368,079 A | 1/1983 | Rugg et al. | |
| 4,440,635 A | 4/1984 | Reiniger | |
| 4,461,648 A | 7/1984 | Foody | |
| 4,465,591 A | 8/1984 | Holz et al. | |
| 4,468,256 A | 8/1984 | Hinger | |
| 4,478,644 A | 10/1984 | Berger et al. | |
| 4,483,704 A | 11/1984 | Easter, II | |
| 4,540,467 A * | 9/1985 | Grube et al. | 162/4 |
| 4,540,495 A | 9/1985 | Holloway | |
| 4,566,942 A | 1/1986 | Holz et al. | |
| 4,570,861 A | 2/1986 | Zentgraf et al. | |
| 4,607,797 A | 8/1986 | Enikolopow et al. | |
| 4,632,729 A | 12/1986 | Laakso | |
| 4,637,835 A | 1/1987 | Nagle | |
| 4,650,125 A | 3/1987 | Pellhammer | |
| 4,699,632 A | 10/1987 | Babu et al. | |
| 4,750,437 A | 6/1988 | Rouse | |
| 4,816,117 A | 3/1989 | Pfalzer et al. | |
| 4,836,918 A * | 6/1989 | Szikriszt | 210/151 |
| 4,842,877 A | 6/1989 | Tyson | |
| 4,844,351 A | 7/1989 | Holloway | |
| 4,925,571 A | 5/1990 | Jacob et al. | |
| 4,949,653 A | 8/1990 | Rast | |
| 4,974,781 A | 12/1990 | Placzek | |
| 4,977,943 A | 12/1990 | Miyabe | |
| 5,003,143 A | 3/1991 | Marks et al. | |
| 5,009,370 A | 4/1991 | Mackenzie | |
| 5,013,458 A | 5/1991 | Christy, Sr. et al. | |
| 5,023,097 A | 6/1991 | Tyson | |
| 5,050,375 A | 9/1991 | Dickinson | |
| 5,104,419 A | 4/1992 | Funk | |
| 5,114,488 A | 5/1992 | Huber et al. | |
| 5,116,363 A | 5/1992 | Romweber et al. | |
| 5,119,994 A | 6/1992 | Placzek | |
| 5,122,228 A | 6/1992 | Bouchette et al. | |
| 5,143,481 A | 9/1992 | Schumacher et al. | |
| 5,148,999 A | 9/1992 | Curfman et al. | |
| 5,190,226 A | 3/1993 | Holloway | |
| 5,196,069 A | 3/1993 | Cullingford et al. | |
| 5,196,620 A | 3/1993 | Gustin et al. | |
| 5,217,688 A | 6/1993 | Von Lersner | |
| 5,253,764 A | 10/1993 | Gement | |
| 5,258,293 A | 11/1993 | Lynd et al. | |
| 5,280,757 A | 1/1994 | Carter et al. | |
| 5,300,438 A * | 4/1994 | Augspurger et al. | 435/290.3 |
| 5,361,994 A | 11/1994 | Holloway | |
| 5,412,881 A | 5/1995 | Romweber et al. | |
| 5,427,650 A | 6/1995 | Holloway | |
| 5,427,738 A | 6/1995 | Galloway | |
| 5,429,645 A | 7/1995 | Benson et al. | |
| 5,445,329 A | 8/1995 | Anderson | |
| 5,456,553 A | 10/1995 | Ii et al. | |
| 5,459,071 A * | 10/1995 | Finn | 435/290.2 |
| 5,480,610 A | 1/1996 | Birkholz et al. | |
| 5,492,407 A * | 2/1996 | Gement | 366/228 |
| 5,501,719 A | 3/1996 | Shida et al. | |
| 5,504,259 A | 4/1996 | Diebold et al. | |
| 5,534,437 A | 7/1996 | Arrau | |
| 5,540,391 A | 7/1996 | Anderson | |
| 5,556,445 A | 9/1996 | Quinn et al. | |
| 5,587,157 A | 12/1996 | Cox et al. | |
| 5,589,164 A | 12/1996 | Cox et al. | |
| 5,589,391 A * | 12/1996 | Fink | 435/290.3 |
| 5,602,297 A | 2/1997 | Wang | |
| 5,613,306 A | 3/1997 | Romweber et al. | |
| 5,615,626 A | 4/1997 | Floyd et al. | |
| 5,658,097 A | 8/1997 | Komori et al. | |
| 5,705,216 A | 1/1998 | Tyson | |
| 5,711,817 A | 1/1998 | Titmas | |
| 5,732,892 A | 3/1998 | Neier | |
| 5,772,847 A | 6/1998 | Simpson et al. | |
| 5,795,479 A | 8/1998 | Vogt et al. | |
| 5,822,881 A | 10/1998 | Romweber et al. | |
| 5,844,008 A | 12/1998 | McMillan | |
| 5,879,637 A | 3/1999 | Titmas | |
| 6,123,747 A * | 9/2000 | Kim et al. | 71/8 |
| 6,197,081 B1 | 3/2001 | Schmidt | |
| 6,207,015 B1 | 3/2001 | Templer et al. | |
| 6,238,516 B1 | 5/2001 | Watson et al. | |
| 6,245,195 B1 | 6/2001 | Marwah | |
| 6,267,309 B1 | 7/2001 | Chieffalo et al. | |
| 6,306,248 B1 | 10/2001 | Eley | |
| 6,328,234 B1 | 12/2001 | Saucier et al. | |
| 6,379,527 B1 | 4/2002 | Vogt et al. | |
| 6,397,492 B1 | 6/2002 | Malley | |
| 6,409,841 B1 | 6/2002 | Lombard | |
| 6,458,240 B1 | 10/2002 | Bouchette et al. | |
| 6,730,223 B1 | 5/2004 | Anderson et al. | |
| 7,371,566 B1 * | 5/2008 | Craven, Jr. | 435/290.3 |
| 2005/0166812 A1 | 8/2005 | Noll | |

FOREIGN PATENT DOCUMENTS

| | | |
|---|---|---|
| EP | 0549356 A1 | 6/1993 |
| EP | 1118706 A2 | 7/2001 |
| EP | 1700610 A2 | 9/2006 |
| GB | 809329 | 2/1959 |
| WO | 9212738 A1 | 8/1992 |
| WO | 9323167 A1 | 11/1993 |
| WO | 9426320 A1 | 11/1994 |
| WO | 9732077 A1 | 9/1997 |
| WO | 9947282 A1 | 9/1999 |
| WO | 0072987 A1 | 12/2000 |
| WO | 0224354 A1 | 3/2002 |
| WO | 03025101 A2 | 3/2003 |
| WO | 03035970 A1 | 5/2003 |
| WO | 2006015423 A1 | 2/2006 |

OTHER PUBLICATIONS

United States Patent and Trademark Office, Official Action directed to U.S. Appl. No. 11/296,585, mailed Jul. 22, 2008, 19 pages.

United States Patent and Trademark Office, Official Action directed to U.S. Appl. No. 11/296,586, mailed Sep. 4, 2008, 16 pages.

United States Patent and Trademark Office, Official Action directed to U.S. Appl. No. 10/713,557, mailed Nov. 13, 2003, 9 pages.

United States Patent and Trademark Office, Official Action directed to U.S. Appl. No. 11/296,585, mailed Jan. 21, 2009, 12 pages.

United States Patent and Trademark Office, Official Action directed to U.S. Appl. No. 11/296,585, mailed Jun. 24, 2009, 31 pages.

United States Patent and Trademark Office, Official Action directed to U.S. Appl. No. 11/296,586, mailed Apr. 16, 2009, 11 pages.

International Search Report for PCT/US07/61827.

* cited by examiner

ANGLED REACTION VESSEL

FIELD OF THE INVENTION

The present invention generally relates to processing biomass bearing material including municipal solid waste (MSW), and more particularly relates to reaction vessels for treating biomass bearing material and other material containing cellulose or biomass in a heated and pressurized process.

BACKGROUND OF THE INVENTION

Handling solid waste is an increasingly difficult problem in the industrialized nations. Sixty-one percent of the United States' solid waste is dependent on disposal in landfills. However, nationwide the number of solid waste landfills is falling as the landfills fill to capacity and close, while new landfills cannot be opened due to regulations. The national average for solid waste disposal fees has increased by about 400 percent since 1985. Such fees, called tipping fees, can be expected to raise an average of seven percent per year. In addition, the number of solid waste transfer stations has increased due to the closure of many landfills and the permitting of larger solid waste landfills.

These and other issues pertaining to the environmental impact that landfills will have in the future have prompted solid waste managers to seek methods to reduce volumes and disposal costs of municipal solid waste (MSW). Some experts contend that there is no waste volume problem, but there exists a sorting and recycling problem.

There have been a number of patents for treating and/or reprocessing MSW. These often involve some form of heat and pressure, and often a reaction vessel that may rotate. Although MSW varies in composition, there is a certain norm to its content. Other forms of waste have a biological, fiber, or cellulosic component, and can be processed in the same process that works for MSW or other biomass bearing material. These include sewer sludge, industrial waste streams, industrial byproducts, agricultural waste and byproducts, food processing waste and byproducts, and other sources. Cellulosic material represents approximately seventy percent of the bulk of typical MSW. Other terms for this fraction of MSW have been used, including putricible, organic, and biomass. These terms are considered interchangeable and it is to be understood that the use of the term "biomass bearing material" in this application encompasses MSW as well as all the waste or byproduct streams listed above.

The putrescible, biomass, organic, or cellulosic fraction of biomass bearing material includes all portions that are organic, which could eventually decay in a landfill and the decay could eventually lead to the production of methane gas and leachate. If this cellulosic material can be separated into reusable products, much of the pollution resulting from the disposal of organic bearing waste will be alleviated. Products that can be made from the cellulosic fraction of biomass bearing material include loose or palletized fuel or feedstock for gasification, bio refineries and conversion into ethanol and other chemicals and fuels. The biomass bearing fraction of MSW could also serve as a source of hydrogen and other liquid, elemental or gaseous products achieved through gasification or other thermal processes, including hydrolysis.

Once the cellulosic material is removed, the biomass bearing material is much reduced in volume and other recoverable fractions of the waste stream can be recovered. Ferrous and non-ferrous metals, plastics, and textiles can represent an additional fifteen percent of the remaining biomass bearing material.

There are processes available that can recover each of these materials and send them to their respective market. If the cellulosic and recoverable waste streams are removed from biomass bearing material, the volume of such waste streams going to landfills is typically less than fifteen percent of the original amount. This reduction in volume reduces hauling costs, landfill space requirements. Removal of the cellulosic portion of biomass bearing material also accomplishes this reduction while reducing effluents, including methane and leachate. Further, if the cellulosic portion is removed from the biomass bearing material, the remaining fraction of inorganic waste could be disposed of in waste sites reserved for construction or other inorganic waste, which is space that is often less regulated and therefore less expensive.

Many prior art reaction vessels for treating biomass bearing material utilize fairly high-pressure steam in order to cook and soften the cellulosic fibers of the biomass bearing material. This presents a problem because high-pressure steam vessels require significant licensing and inspection regimes, and must be built to withstand higher pressure. If the reaction vessel can achieve adequate softening, pulverization, and separation of cellulosic fibers while utilizing low pressures, the vessel could be lighter, less expensive to construct and operate. A lower pressure reaction vessel that achieves adequate softening, pulverization, and separation of cellulosic fibers is thus needed.

What is also needed is a reaction vessel that incorporates condensation of gaseous affluent steam from the reaction vessel. This condenses steam from the vessel, and also reduces or eliminates unpleasant gas emissions from the vessel.

There is also a need in the industry to provide a vessel and processing system that results in a product with fairly low moisture content, provides a sterilization effect upon the biomass bearing material, imparts a chemical change to the biomass bearing material and imparts beneficial handling, flow, and chemical characteristics to the product of processing in the reaction vessel, which thus converts the biomass from a waste into a feedstock for subsequent processes. Additionally, the non biomass fractions can benefit by removing labels from containers, fracturing glass for possible later separation from the waste stream, compacting and agglomerating plastics, and compacting ferrous and non-ferrous materials.

SUMMARY OF THE INVENTION

The treatment vessel of the present invention achieves these and other objectives. The vessel includes a generally cylindrical reaction vessel with a first end and a second end. The vessel is configured for rotation, which is achieved through the use of one or more support tracks, wheels, and trunnion assemblies to support the reaction vessel as it rotates. It also has a drive mechanism for powering the rotation of the reaction vessel and its contents. The vessel can be set at different angles from the horizontal, including at about 3 to 10 degrees, or preferably 4 to 8 degrees.

The biomass bearing material treatment vessel of the present invention includes an access opening through which biomass bearing material may be loaded into and removed from the reaction vessel. The reaction vessel includes a door assembly, which is adjacent to the access opening, for closing the access opening and holding the door closed against pressure from within the vessel. The description of the material to be processed in the vessel will be described as biomass bearing material, with the understanding that this refers to any waste or by product stream containing fibrous, cellulosic, or biomass material, including streams otherwise described further as organic, putricible, municipal solid waste, and including sewer sludge, industrial waste and by product streams, agricultural and food processing streams, and other cellulose or organic bearing streams.

The biomass bearing material treatment vessel includes one or more flights of auger vanes on the interior wall of the reaction vessel for moving biomass bearing material from the first end to the second end of the vessel. The flights, through rotation of the vessel, cause the biomass bearing material to move from one end of the reaction vessel to the other and back again towards the door opening. The auger vanes have a base edge, which is attached to the interior vessel wall, typically by welding. Of course brackets or studs or other known attachment methods can also be used for this purpose.

The auger vanes also have a top edge, with the top edges of the auger vanes defining a bore parallel to the long axis of the reaction vessel. The bore has a diameter that is approximately one third of the diameter of the reaction vessel, when seen in cross section or end view. This means that the space defined by the auger vanes occupies about two thirds of the cross sectional diameter of the reaction vessel.

An optional feature of the reaction vessel is that it includes a number of paddles which are attached to the top edge of the auger vanes. Structures called rods or posts are attached to the top edge of the auger vane and extend toward the interior of the reaction vessel and away from the top edge of the auger vane. To the supporting posts are attached paddles which are generally rectangular in shape. The paddles are spaced apart from the top edge of the auger vanes and the paddles have a top edge which is closest to the center line of the reaction vessel. The top edges of the paddles form the bore of the reaction vessel, with the bore having a diameter that is approximately 1/3 the diameter of the reaction vessel when seen in cross-section or end view.

The reaction vessel also includes one or more sparging lines which deliver steam into the interior of the reaction vessel for heating the biomass bearing material, softening the fibers of the cellulosic waste, and adding pressure to the interior of the vessel. The steam is administered to the sparging lines through a fitting that rotates as the reaction vessel rotates.

A feature of the reaction vessel is a number of raised projections that extend from the top edges of auger vanes. As the reaction vessel turns and biomass bearing material tumbles within the auger vanes, the raised projections on the top edges of the auger vanes aid in moving, pulverizing, and shredding the biomass bearing material. These raised projections can be generally trapezoidal or triangular in shape, with one edge attached to the auger vane top edge. If triangular, the point of a triangle projects away from the top edge of the auger vane.

The raised projections can also be oriented in a plane generally normal to the plane of the auger vane. This results in raised projections perpendicular to the auger vane and parallel to the long axis of the reaction vessel. These projections can point in one or both directions from their attachment point on the auger vane top edge, resulting in jagged teeth pointed backward and forward perpendicular to the general orientation of each auger vane.

The auger vanes can be constructed to be one or more continuous spirals from one end to the other of the reaction vessel. The auger vanes can also be broken into a series of arching vanes, with each section welded or otherwise attached to the interior wall of the reaction vessel and contributing to the auger effect during rotation of the vessel.

The reaction vessel can be considered to have three sections. The first section is adjacent to the access opening. The second section is positioned in the middle of the reaction vessel. The third section is positioned at the end of the reaction vessel opposite the access opening. The most important location for the paddles or raised projections is in the third section of the reaction vessel. Thus, a reaction vessel could be built with paddles or raised projections in the third section, or in the third and second sections, or in all three sections of the reaction vessel.

The reaction vessel includes a steam injection system by which steam is injected into the vessel via steam tubes that run along the sides of the reaction vessel parallel to the long axis of the reaction vessel. Thus, the steam sparging tubes penetrate the auger vanes where the auger vanes are attached to the vessel wall. The steam sparging tubes receive their steam from a circular steam manifold that connects to all of the steam tubes. The steam manifold rotates with the vessel and is attached to a rotary joint through which steam is injected into the steam manifold and the vessel. The steam sparging tubes can extend the entire length of the vessel and can extend out the end of the vessel opposite from the end in which the steam is injected. The steam sparging tubes include orifices through which steam is introduced to the interior of the vessel.

The biomass bearing material treatment vessel may also include an effluent condensation system. Part of the effluent condensation system is a steam eductor. The steam eductor operates on the principal that when air is blown into a cone, it creates a vacuum. In this case, the vacuum pulls the steam, previously injected into the vessel, from the vessel into a condensing chamber where condensation takes place.

The condensation system is achieved by putting the steam from the processor in contact with a cooler media that will cause the steam to cool and condense. The condensing of the steam thus creates a vacuum.

The biomass bearing material treatment vessel includes a swing-away door assembly, which is adjacent the access opening. The door assembly includes a swing-away door, which covers the access opening, and a davit assembly for supporting the swing-away door. The davit assembly includes a generally vertical davit upright, which supports the door through a generally horizontal door support arm. The support arm has a first end and a second end with a counterweight attached to the first end and the access opening door attached to the second end. The davit assembly is configured to rotate around the davit upright so the access opening door may be rotated away from or toward the access opening. This can be accomplished by manual rotation of the davit assembly or it can easily be automated.

The biomass bearing material treatment vessel may further include one or more chain sections that are attached to the interior of the vessel. These may be attached in various lengths, but typically two to six feet is sufficient to accomplish the purpose, while three to four feet has also proven effective. The chains would be sized according to the size and capacity of the reaction vessel, but a thickness of 3/4 inches has proven successful for one preferred embodiment. The chains are attached so that they hang freely in the biomass bearing material treatment vessel. A chain detachably attached to the auger vane about every six feet is a preferred configuration. When the vessel rotates, the chains assist in agitating, pulverizing, and mixing the biomass bearing material contained within the vessel.

The vessel is configured to rotate in one direction to load, pulverize, and heat process the biomass bearing material. The rotation of the reaction vessel is then reversible to further pulverize and move the biomass bearing material toward the access opening end for removal of the biomass bearing material through the access opening.

The door sealing system of the vessel includes a first raised locking rim, which surrounds the access opening. This first raised locking rim corresponds with a second raised locking rim, which surrounds the access opening door, which will be referred to as simply the door. When the door is placed adjacent the access opening, the first locking rim is side-by-side with the second locking rim, which is on the door itself. The door sealing system includes a clamp collar for sealing the two locking rims together. Thus, it holds the access opening door over the access opening. The clamp collar can further include a first section and a second section with one or more joining devices for joining the two sections together. The joining devices can be one or more clamp screws that draw the first and second clamp sections and thus hold them together until released. The clamp screws move through threaded bosses on the sides of the clamp collar sections. The door closing assembly can comprise two clamp screws, which are mounted on corresponding bosses on the sides of the first and second clamp sections. These are driven by one or more motors to pull the collar sections together through the use of threaded screws.

The first and second locking rim can each include a bevel. The first bevel surface would be located on a side opposite the contact surfaces of the locking rims. The second bevel surface would be located on the second locking rim also on the side of the locking rim away from the contact surface. The clamp collar sections can include a corresponding angled surface, which would interact with the first and second bevels of the first and second locking means. As the clamp collar sections close on the locking rings, the angled surfaces would tend to guide the door into alignment with the access opening.

The biomass bearing material is loaded into the reaction vessel and moved away from the access opening through rotation of the reaction vessel and its auger vanes. When sufficient biomass bearing material is loaded into the reaction vessel, the reaction vessel is closed and the ambient atmosphere inside the vessel is purged by steam from the sparging lines. When the ambient air is evacuated, the vessel is sealed and the pressure buildup begins. Then, steam is injected into the reaction vessel and heat and pressure slowly builds up. An internal pressure of less than fifteen pounds has been found to be suitable for the purposes of this method, and advantageous because it would not be classified as a pressure vessel. However, use of higher steam pressures is also a possible variation of the process. The reaction vessel is rotated, while steam is injected for a period of time to soften the fibers of cellulosic waste within the biomass bearing material. Steam is injected at fifteen pounds or less, or as high as 55 pounds, through the steam sparging lines in the vessel. Although the method can operate under varied conditions depending on the particular blend of biomass bearing material being treated, a reaction time of approximately fifteen to forty-five minutes has been found to be sufficient to soften the fibers of most biomass bearing material and to achieve good sterilization. After this time has been reached and sufficient time has been allowed for churning, shredding, and pulverizing the biomass bearing material, the steam is evacuated through the use of a steam eductor system. The steam eductor system includes an air nozzle and operates by airflow through an orifice that creates a vacuum.

The internal atmosphere from the vessel is thus removed through a barometric condenser before the vessel is opened in order to reduce the volume of escaping emissions from the vessel. After evacuation is accomplished, the door is removed and the processed material, hereinafter called feedstock material, is removed by rotation of the vessel and propelled by the action of the auger vanes. The feedstock material at this point has been chemically altered and is no longer biomass bearing material in terms of chemistry or physical characteristics. As feedstock, it is ready for use in any number of operations which require a cellulose or carbon based feedstock. After being removed from the reaction vessel, the feedstock material is treated for separation of the cellulosic fiber components from other materials such as plastic, aluminum, glass, and various metal components. The separation processes that are well known in the industry separate each of these streams, which is the subject matter of other patents and practices.

Another aspect of the invention is a feedstock and a process for making a feedstock for other operations, the feedstock being made from the vessel of the invention. After processing in the vessel the feedstock material is chemically and physically different than the biomass bearing material which was placed in the reaction vessel, and is a superior feedstock for many applications including as a bio-energy product of various kinds. The feedstock material is a superior feedstock for processes that convert fibrous materials into a liquid, solid or gaseous bioenergy product and can be further subjected to other processes or treatments for production of similar or subsequent products and can be further subjected to other process or treatments for production of similar or subsequent products. The change in the biomass bearing material into a feedstock is due to a chemical reaction of the cellulosic portion of the feedstock material in the reaction vessel, and is not just a separation process. In this reaction, the cellulose and hemicellulose molecules of the fibrous portion of the feedstock material are broken down and formed into simpler compounds. These compounds have less crystallinity than the original cellulose and hemicellulose constituents of the fibers.

Because of an increased surface area and homogenous sizing caused by the action of the process, the feedstock is effective for use in gasification. The produced gas can be utilized as a substitute for natural gas or can be compressed or liquefied. The produced gas, or "syngas", could also be stripped of various elements, including hydrogen. The syngas can also be converted by other methods into ethanol, "bio oils" and other chemicals or energy sources. Alternatively, the feedstock can be used in the process of hydrolysis, whereby the feedstock is used to produce sugars for distillation and other uses. The feedstock can also serve in a solid energy product, in which free flowing solids or pelletized or granular feed are burned for energy Another process for which the feedstock material of the invention is suitable is as furnish. Furnish is a fibrous product which is used as a feedstock in the paper industry. Furnish is fed into the paper making process and also used to make insulation, absorbents, corrugation, fireproofing, and many other pulp products.

Further, the purpose of the foregoing abstract is to enable the United States Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measure by the claims, nor is it intended to be limiting as to the scope of the invention in any way Still other features and advantages of the present invention will become readily apparent to those skilled in this art from the following detailed description describing only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive in nature.

DESCRIPTION OF THE PREFERRED EMBODIMENTS

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

Figure 1:
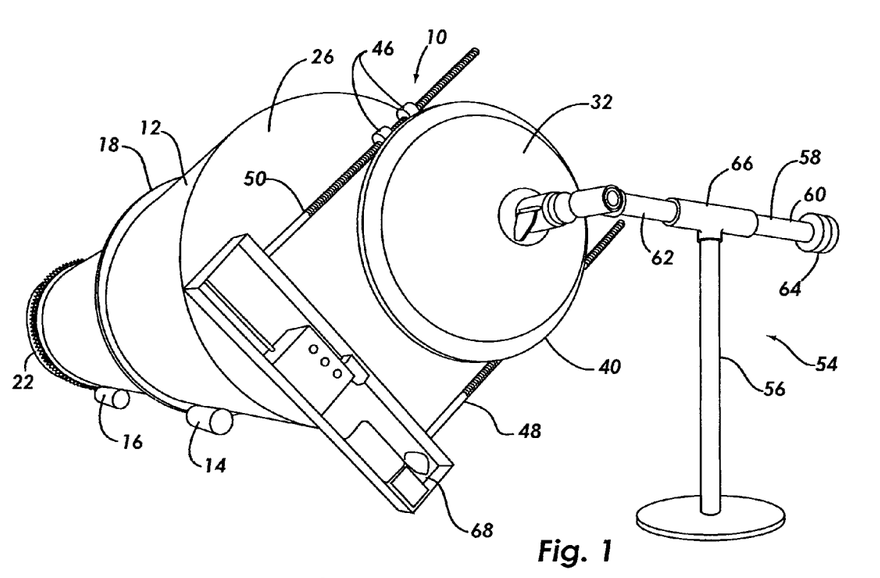
FIG. 1 is a perspective view of the Biomass bearing material processing vessel.

Some of the preferred embodiments are shown in the FIGS. 1 through 12. FIG. 1 shows the biomass bearing material treatment vessel 10. It includes a reaction vessel 12. In one preferred mode of the invention, a first trunnion assembly 14 and a second trunnion assembly 16 supports the reaction vessel 12. The trunnion assembly includes a track 18 and a trunnion 20. These components can be sized according to the size of a specific reaction vessel. However, in a preferred embodiment of the vessel, the trunnions are cylinders of solid steel approximately fifteen inches in diameter and approximately ten inches in length. The vessel 10 is preferably tilted at an angle, and may be configured to have an adjustable angle. For fixed angle versions, an angle from 2 to 10 degrees is preferred. More specifically, an angle of 4 to 8 degrees is desirable, and an angle of approximately 6 degrees is optimal.

The reaction vessel also includes a gear ring 76, which is driven by a motor 80 and a drive gear 78. A preferred embodiment of the gear ring 78 is approximately ten inches wide and is made of steel approximately five inches thick. While a geared drive system is preferred, other drive systems would also work, including a chain and sprocket drive or a cradle formed by a chain and sprocket under the vessel.

The reaction vessel 12 can take a number of configurations with different sizes depending upon the desired capacity and throughput of the operation. One preferred configuration of the reaction vessel is approximately fifty feet long and ten feet in diameter. It is made generally of one-half inch steel plate with one and one-fourth inch reinforced steel plate in the region of the trunnion assemblies 14, 16 and the track 18. The reaction vessel has a rounded ellipsoidal head at the second end 22 of the reaction vessel. At the first end 24 of the reaction vessel, the vessel tapers from approximately a ten foot diameter to approximately a six foot diameter opening on a frustoconical section approximately five feet in length. A cylindrical collar 28 with a first locking ring 30 is at the narrow end of the frustoconical section 26. Shown adjacent the first locking ring 30 in FIG. 1 is the door 32, which includes a second locking ring 34.

Figure 7:
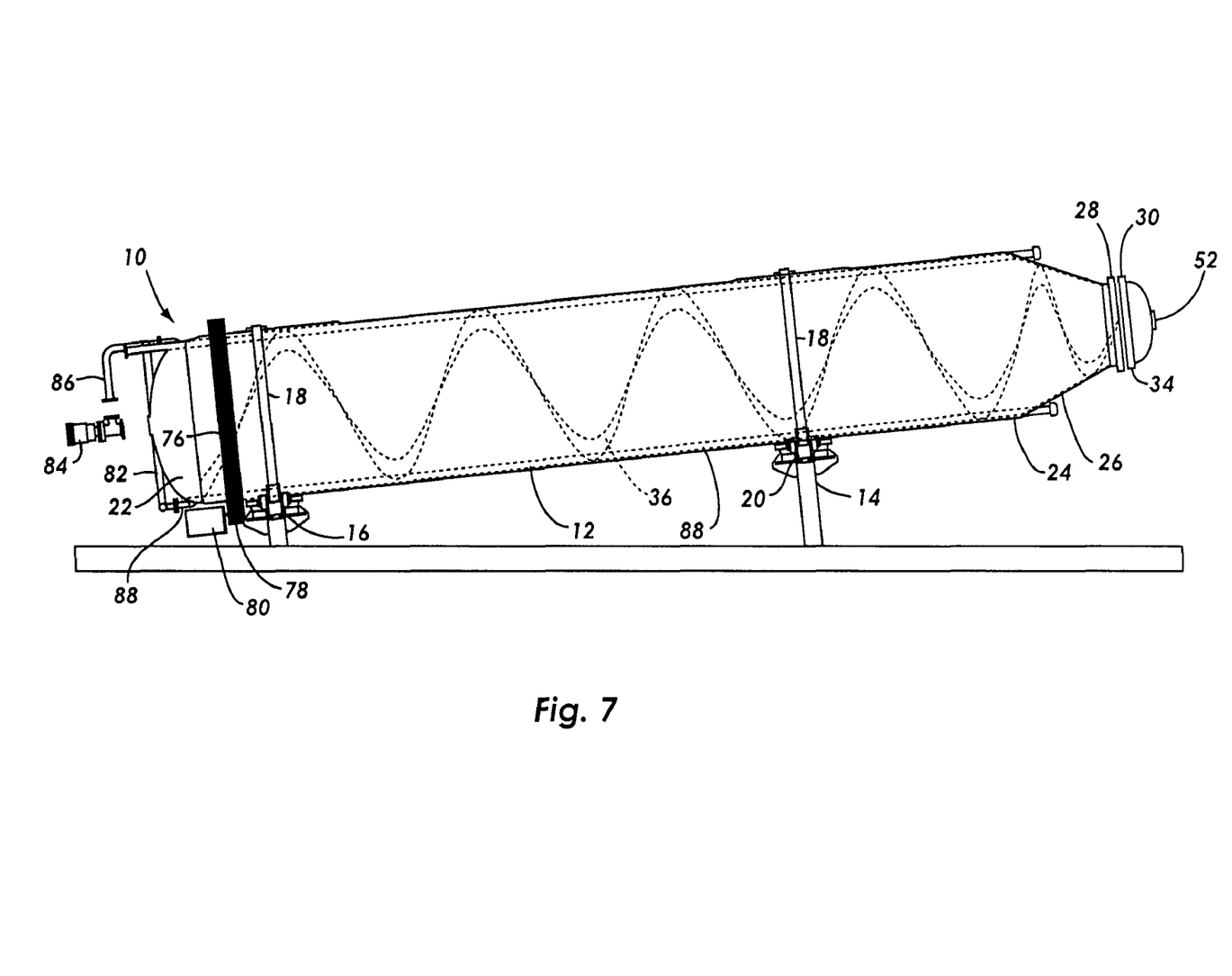
FIG. 7 is an elevation view of the reaction vessel.

A spiraling auger vane 36 is inside the reaction vessel 12. This is preferably made of three eights inch thick steel, welded at its base edge to the interior of the reaction vessel wall. The top edge of the auger vane 36 extends away from the reaction vessel wall towards the center of the reaction vessel 12. Although the auger vane 36 is shown in FIG. 7 as being one continuous spiral from the first end 24 to the second end 22, the auger vane 36 could also be constructed of multiple spirals or several disconnected sections, which together form a spiraling configuration attached to the inside wall of the reaction vessel 12. The auger vane can be attached to the interior vessel walls by welding or by attachment to brackets mounted to the interior vessel wall, or by other conventional means of attachment. Mounting by brackets would allow easier replacement of the vane sections.

Figure 2:
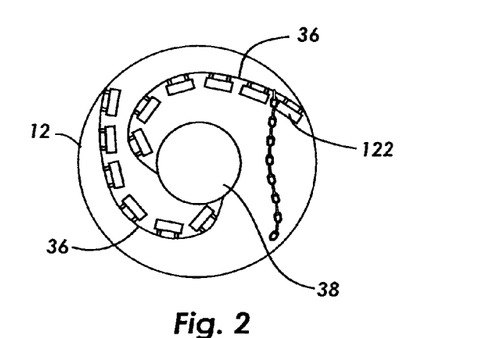
FIG. 2 is a cross-sectional view of the second end of the Biomass bearing material processing vessel.

In one preferred embodiment of the present invention, the auger vanes extend into the interior of the reaction vessel 12 and their top edges form the outline of a bore 38. The diameter of the bore 38 is approximately one-third of the diameter of the reaction vessel of a particular cross section of the reaction vessel. FIG. 2 shows such a cross section of the reaction vessel with the bore 38 being approximately one-third the diameter of the vessel 10.

Figure 9:
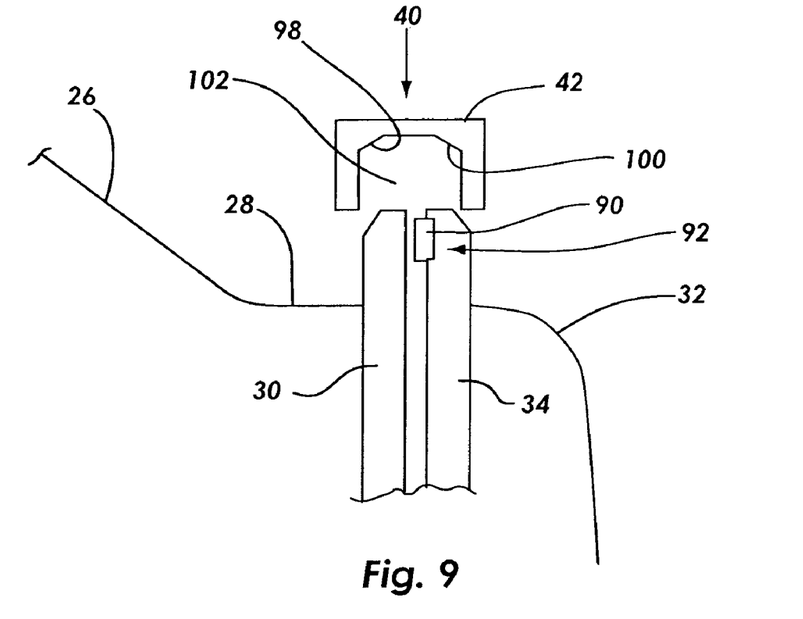
FIG. 9 is a view of the closing action of the door assembly.
Figure 10:
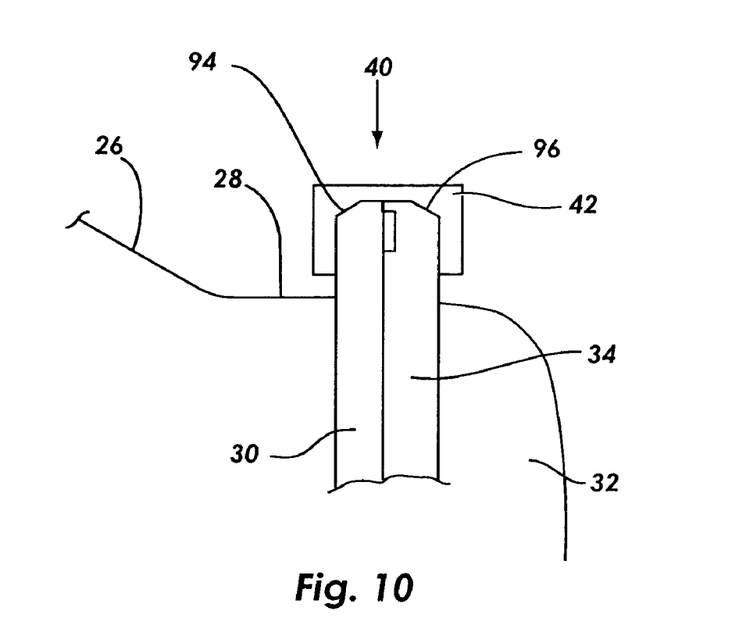
FIG. 10 is a view of the door closed against the access opening.

FIG. 1 shows the door 32 of the vessel. The door 32 is also seen in FIGS. 3, 4, 7 and 8. In the preferred mode, the door 32 is approximately six feet in diameter and, as shown in FIG. 7, is ellipsoidal in cross sectional shape. The door 32 includes a second locking ring 34. The door is closed to the access opening by a clamp collar 40. In the preferred embodiment of the invention, the clamp collar is made of a semicircular first section 42 and a semicircular second section 44. On each of the clamp sections are two threaded bosses 46. Each of these correspond with the threaded bosses on the opposite clamp collar section. A first and second clamp collar screw 48 and 50 pass through the threaded bosses 46 on the clamp collars. When the screws 48, 50 are turned, the first and second sections of the clamp collar 40 are drawn together. This locks the door 32 to the access opening 52 of the reaction vessel 10. FIGS. 9 and 10 show this closing operation more closely. In one preferred embodiment of the invention, the clamp collar screws are approximately one and one-fourth inch in diameter and approximately twenty-five inches in length.

The preferred embodiment of the invention includes a davit assembly 54, as shown in FIG. 1. The davit assembly 54 includes a davit upright 56 and a door support arm 58 with a first end 60 and a second end 62. A counterweight 64 is attached to the first end 60 of the door support arm 58. The door 32 is attached to the second end 62 of the door support arm 58. The configuration of the components of the davit assembly 54 would vary in size depending on the size of the insulation and the size of the door 32 they were associated with. One particular configuration that has proven successful is one with the davit upright being made of approximately six inch diameter tube with the door support arm 58 being made of approximately four inch diameter steel tube. The counterweight in this configuration will vary to match the weight of the associated door 32, but in one preferred embodiment, the counterweight 64 is made of steel and weighs approximately 250 pounds. The door support arm 58 attaches to the davit upright 56 by means of a T-connection 66. The T-connection 66 is rotatable about the davit upright 56 and includes a bearing (not shown) for rotation. The bearing can be a sleeve in which the davit assembly rotates. The davit assembly can be mounted with the base in any configuration. The davit can remain attached to the door during the entire process.

Figure 8:
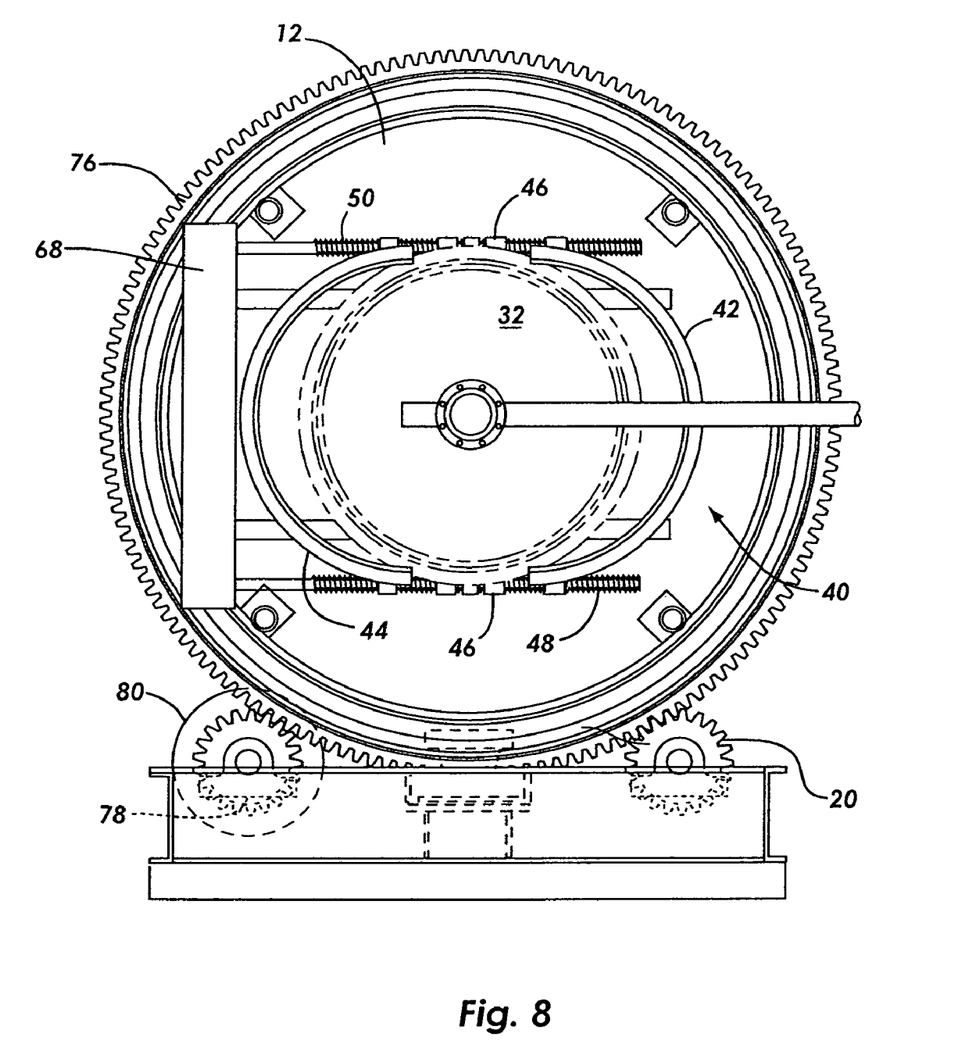
FIG. 8 is an end view of the reaction vessel.

In one preferred embodiment of the invention, the first and second clamp collar screws 48 and 50 are turned by one or more motors that are located in a motor housing 68, as shown in FIG. 8. A motor of approximately three horsepower operating through a gearbox is sufficient for this task.

Figure 3:
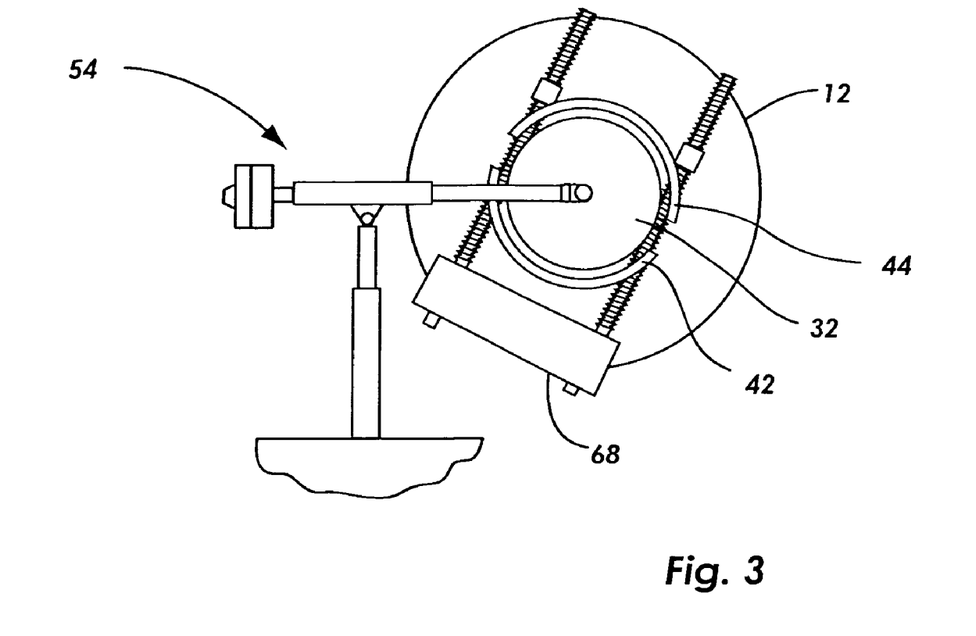
FIG. 3 is front view of the davit and door assembly.

FIG. 3 shows a front view of the davit assembly 54 attached to the door 32. In this view, the first section clamp collar 42 and the second section clamp collar 44 are in the open position, so that the door 32 may swing away from the access opening 52.

Figure 4:
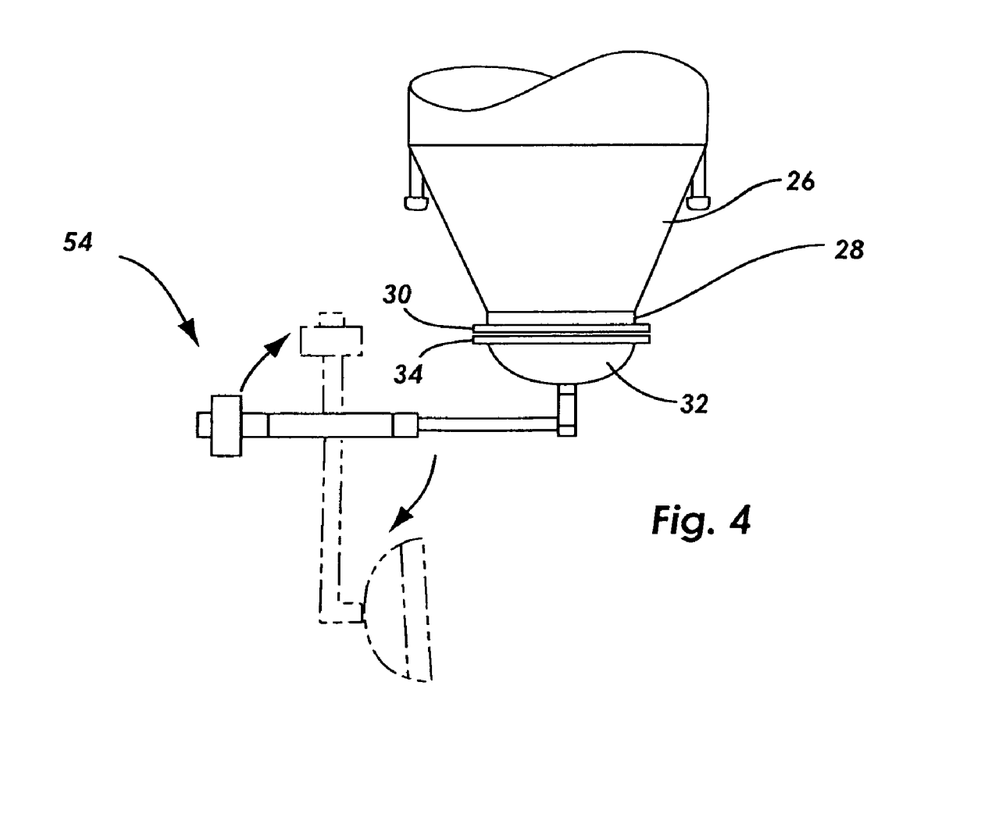
FIG. 4 is a top view of the davit and door assembly.

FIG. 4 shows a top view of the davit assembly 54. In the position shown in solid lines, the davit assembly 54 and the attached door 32 are in a closed position. The door is positioned adjacent the first locking ring 30, which surrounds the access opening on the cylindrical collar 28. Cylindrical collar 28 is attached to the frustoconical section 26.

Figure 5:
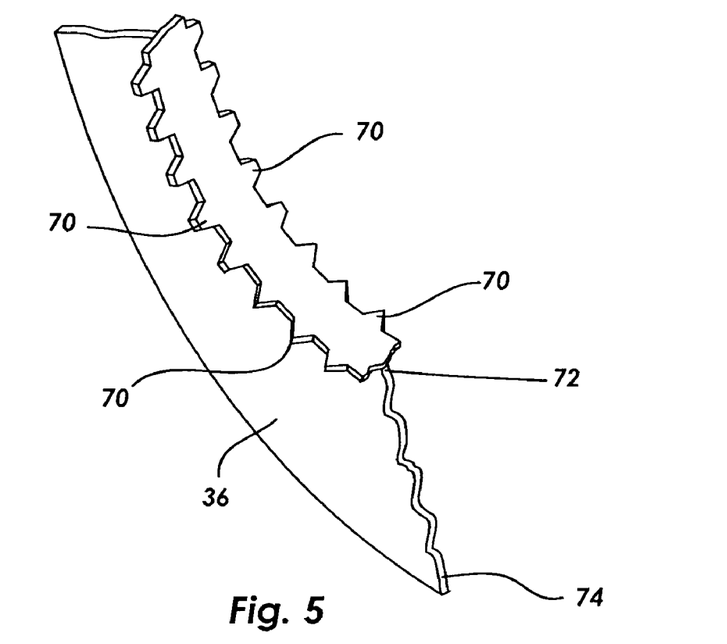
FIG. 5 is a perspective view of an auger vane with projections.
Figure 12:
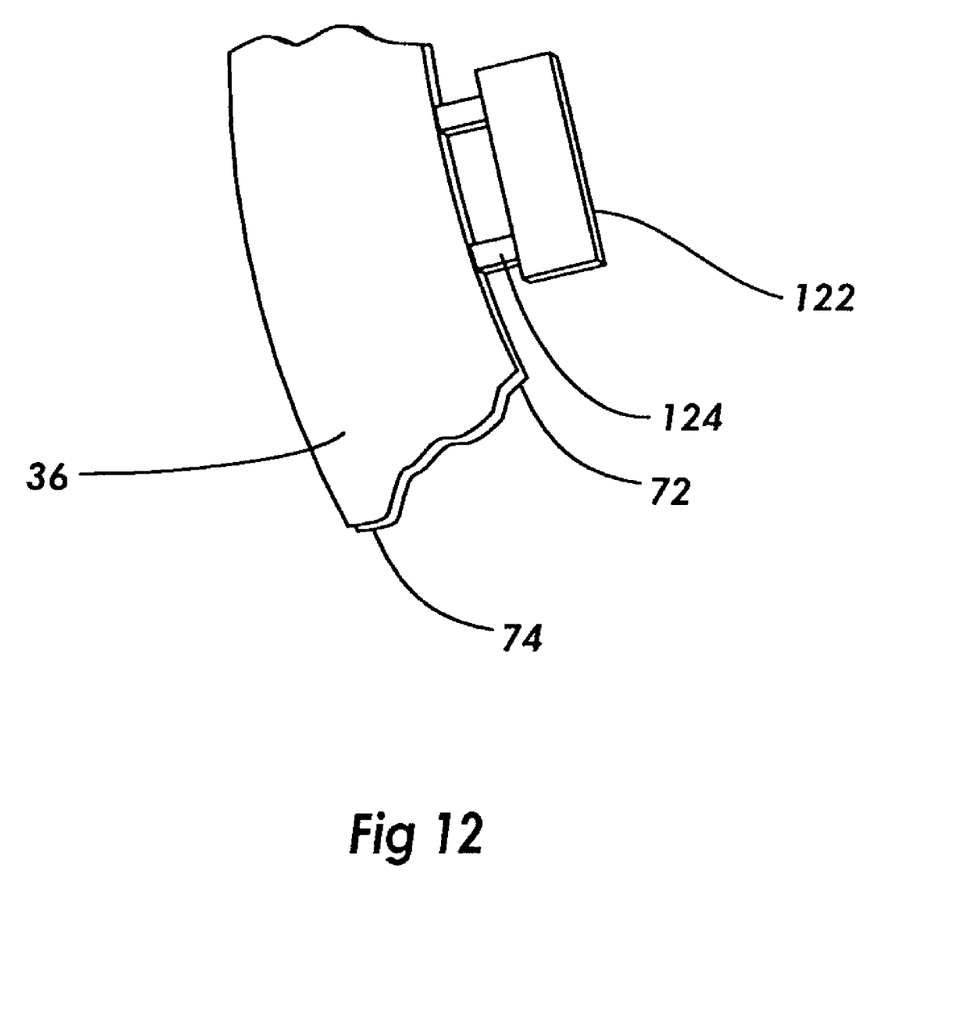
FIG. 12 is a perspective view of an auger vane with paddle.

A preferred embodiment of the invention can include raised projections that extend from the edges of the auger vanes 36, as shown in FIGS. 2, 5, and 12. These can extend vertically or horizontally from the top edge of the auger vanes. A preferred embodiment is with projections extending in both directions perpendicular from the auger vanes 36. Such projections can be triangular, trapezoidal or other shapes to form a jagged cutting edge. If trapezoidal or triangular, they can extend approximately one inch from the auger vane 36 to which they are attached, with a base edge of approximately one inch. If trapezoidal, the edge parallel to the base edge can be three-quarter of an inch in width. The projections are preferably approximately one-quarter inch thick steel welded to the edge of the auger vanes. FIG. 5 shows trapezoidal projections attached to the auger vane edge. FIG. 5 shows a perspective view of a section of auger vane 36 of the present invention. Attached to this section of auger vane 36 are a number of raised projections 70 that are joined together as a unit and mounted to top edge 72 of the auger vane. The base edge 74 of the auger vane is welded to the interior wall of the reaction vessel 12. A number of these projections are attached to the top edge of the auger vane and can be parallel with the auger vane or, as shown in FIG. 5, can be perpendicular to the auger vane and pointing in both directions. As the auger vane turns, biomass bearing material is pushed against the auger vane and projection 70 and tumbled from one section of the reaction vessel 12 to another. This allows the raised projections 70 help shred and pulverize the biomass bearing material. This is especially true after the biomass bearing material has been subjected to heat and steam, and the cellulosic fibrous materials are soft and shredable.

The projections can take another form, as shown in FIGS. 2 and 12. Another preferred configuration of the auger vanes 36 is to have shorter vanes to which are attached paddles 122. The paddles 122 are joined to the auger vanes 36 by posts 124. The size of the paddles 122 and the posts 124 could take many configurations depending on the size of the vessel being built. In the case of a reaction vessel, which is approximately 50 feet long, the vanes and paddles, could be constructed using paddles which are approximately 18 inches wide and 60 inches long, attached by posts 124 which are approximately 24 inches long. The paddles can also form a widened region of the auger vanes 36. If placed on the posts 124, the paddles 122 would be spaced apart from the top edge 72 of the auger. The top edge of the paddle 122 would form the periphery of the bore inside the vessel as shown in FIG. 2.

Figure 6:
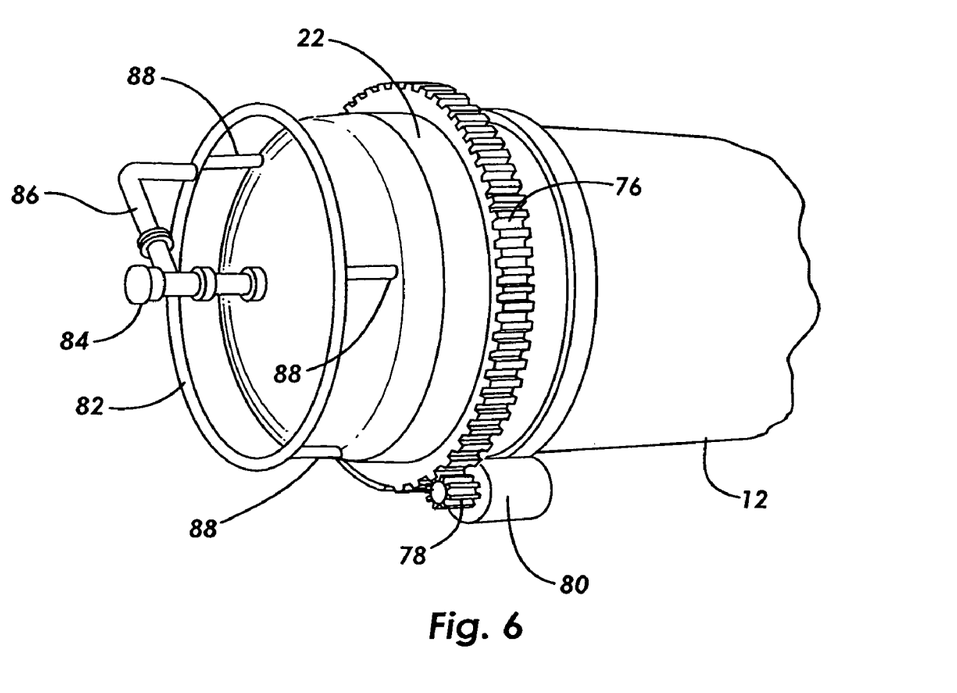
FIG. 6 is an end view of a cross section of the vessel.

FIG. 6 is a view of the second end 22 of the reaction vessel 12. In one preferred embodiment of the present invention, a gear ring 76 interacts with a drive gear 78 and a motor 80 to rotate the entire reaction vessel 12. Also seen on the second end 22 is a rounded ellipsoid head. Steam is injected into the vessel through a circular steam sparger manifold 82. Steam is injected into the sparger manifold 82 by means of a rotary joint 84 and a steam connector line 86. From the sparger manifold 82, a number of sparger lines 88 extend into the interior of the reaction vessel 12. In this configuration, these sparger lines are straight and attached to the interior wall of the reaction vessel 12. These lines are also shown in FIG. 7. While they are shown in FIG. 7 as protruding through the opposite end of the reaction vessel 12 and being terminated there, the ends of the sparging lines 88 could also be linked to each other so that if an obstruction blocked one sparging line, the line could be pressurized beyond the obstruction from the other end. A desirable feature is a steam outlet on the access door of the vessel, and valving which allows use of the rotary joint for evacuation of steam from the vessel.

FIG. 7 is an elevational view of the biomass bearing material treatment vessel 10. Shown is the reaction vessel 12 with a first trunion assembly 14 and a second trunion assembly 16. The reaction vessel 10 is held at an angle from 2-10 degrees, depending on the selections of the operator. The first end 24 of the reaction vessel includes a frustoconical section 26, a cylindrical collar 28, and a first locking ring 30. Auger vanes 36 are shown attached to the inner wall of the reaction vessel and form a spiral the length of the reaction vessel 12. The height of the auger vane decreases towards the first end 24. At the second end 22 of the reaction vessel, a circular steam sparger manifold 82 is seen. This connects to a steam connector line 86 and a rotary joint 84. A number of sparger lines 88, which extend into the reaction vessel 12, extend from the steam sparger manifold 82. Orifices (not shown) in the sparger lines 88 allow steam to exit the sparger lines into the reaction vessel 12.

The first trunion assembly 14 includes trunions 20 and tracks 18, which circumvolve the reaction vessel 12. The reaction vessel 12 is turned by a motor 80, which drives a drive gear 78 that interacts with a gear ring 76 attached to the reaction vessel 12, causing the reaction vessel 12 to rotate on the trunion assembly. It is to be understood that although two trunion assemblies 14,16 are shown, a pair of trunions at each trunion assembly supports the reaction vessel 12. Thus, each tract is supported by two trunions, and in this embodiment, the reaction vessel is supported by four trunions.

FIG. 8 shows an end view of the first end 24 of the reaction vessel 12. Shown is the gear ring 76, which circumvolves the reaction vessel 12. The door 32 is shown in its position covering the access opening. The first section 42 of the clamp collar is shown, as well as the second section 44 of the clamp collar. The first clamp collar screw 48 and the second clamp collar screw 50 are shown. The clamp collar 40 is shown in an open position in solid lines and in a closed position in dashed lines. As shown, the clamp collar screws 48 and 50 extend from a motor housing 68 in which preferably two separate motors turn the clamp collar screws and cause the sections of the clamp collar to come together or move apart. Trunnion 20 is shown supporting the reaction vessel 12. Also shown is drive gear 78, which is driven by a motor 80.

FIG. 9 is a cross sectional side view of the door locking action of the reaction vessel. Shown is a portion of frustoconical section 26 and cylindrical collar 28 of the reaction vessel. The first clamp collar section 42 is shown. Also shown is the first locking ring 30 and the second locking ring 34, which is attached to the door 32. As shown in FIG. 9, the door 32 is adjacent to but not sealed against the first locking ring 30. The first section clamp collar 42 is adjacent to but not engaged with the first and second locking rings 30 and 34. The second section clamp collar 44 would be similarly positioned. As the first section 42 of the clamp collar moves down and around the first and second locking rings 30 and 34, it moves into the configuration shown in FIG. 10. In FIG. 10, the first section clamp collar 42 has moved into engagement with the first locking ring 30 and the second locking ring 34. The first locking ring 30 includes a bevel surface 94 and the second locking ring 34 includes a bevel surface 96 to assist in positioning the door. In the position shown in FIG. 10, the clamp collar has forced the two locking rings together and holds them together in a sealed configuration. A gasket 90 is present in a recess 92 in the second locking ring 34. The bevel surfaces 94, 96 interact with corresponding beveled surfaces 98, 100 in the interior channel 102 of the first clamp collar 42. Although only one clamp collar is shown, it is to be understood that the preferred embodiment of the invention utilizes two semicircular clamp collars which bring the door into sealed engagement with the access opening as shown in FIGS. 9 and 10.

Figure 11:
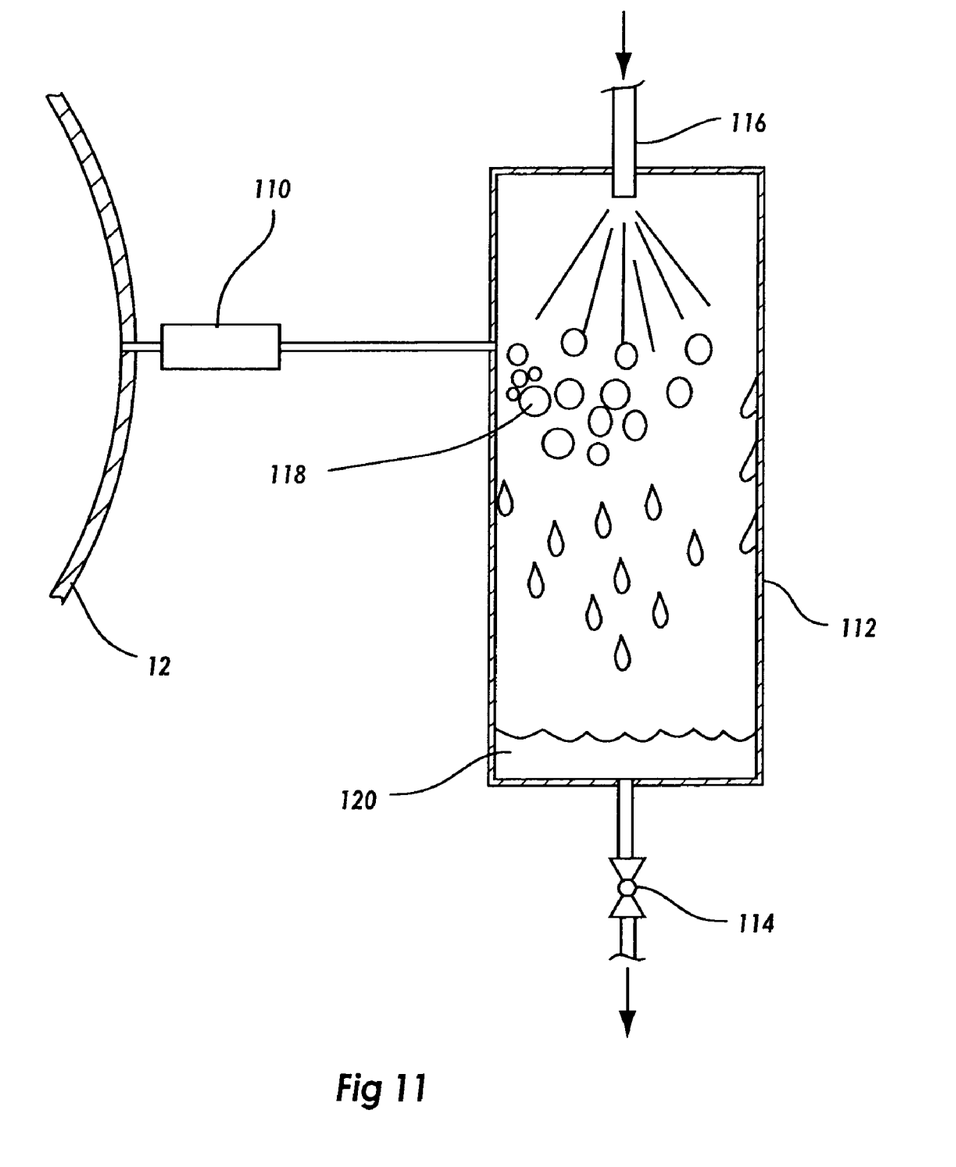
FIG. 11 is a view of the effluent system.

FIG. 11 shows a view of the effluent system. The effluent system in the processing vessel of the invention includes a steam eductor 110 and a barometric condenser 112. The barometric condenser 112 can take various forms and would of course be sized according to the particular design of the reaction vessel 12. One version of the barometric condenser 112 can include a condensation tank, which is approximately three feet in diameter and six feet tall, and is oriented vertically. A connection between the tank and the reaction vessel is made so that steam from the reaction vessel can be allowed to enter the tank at a point about two thirds from the bottom of the tank. As the steam 118 from the reaction vessel enters the tank, it is condensed. This can be done in several ways. A very effective method is to spray water 116 from the top of the tank onto the steam 118. This not only condenses the gaseous steam into a condensate liquid 120, but in doing so, also creates a vacuum, which pulls more steam from the reaction vessel. One effect of this is that the volume of effluents from the barometric condenser 112 is increased, and the concentration of contaminants from the steam is decreased. There is also a drain valve 114 for removing the condensate 120.

Other methods of condensing water from the steam are also possible, such as having the steam hit tubes filled with a cool liquid, which would require a refrigeration unit to keep the liquid in the tubes cool. Cold air can also be injected into the condensation tank, which would result in less volume of eventual effluent, but with a higher concentration.

The steam eductor is the device that extracts the atmosphere from the reaction vessel and directs it into the barometric condenser. The steam eductor can take a number of forms including an air pump, venturi tube or any other commonly used device that moves air. The steam eductor would be utilized to remove as much steam from the reaction vessel as possible before it is opened. The removal of this atmosphere can continue until there is a negative pressure in the reaction vessel.

Even with a thorough evacuation and flushing of the atmosphere from the reaction vessel, when the door to the reaction vessel is opened and the feedstock material is moved by the augers to the opening, the act of stirring, tumbling, and moving the feedstock material by the reaction vessels and the augers, the feedstock material will release significant quantities of steam. To capture this steam, a hood, which is placed over the door to the reaction vessel so that effluents from the feedstock material can be enclosed in the hood and drawn off to the barometric condenser, is useful. After processing, the biomass bearing material in the reaction vessel is referred to as feedstock, to reflect the change in the physical and chemical makeup of the material. Typically, the feedstock and non-cellulosic material from the reaction vessel are directed to a trommel screen for sorting of the material. While the recently heated feedstock is on the trommel screen and being moved, steam will continue to be released. A hood over the trommel screen is effective at this point to contain steam and gaseous effluents, and to allow them to be channeled to the barometric condenser.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

I claim:

1. A biomass bearing material treatment pressure vessel, comprising:
   a generally cylindrical reaction vessel having first and second ends, said reaction vessel configured for rotation;
   a drive mechanism for causing rotation of the reaction vessel;
   one or more support tracks and wheels for supporting said reaction vessel as it rotates;
   at least one access opening to an interior of said reaction vessel, and through which biomass bearing material may pass;
   a door for closing said access opening;
   a door sealing system operatively associated with said door for sealing said door to said vessel at said access opening and for maintaining a pressure differential between the interior of said vessel and an exterior thereof;
   at least one flight of auger vanes on an interior wall of said reaction vessel and extending into the interior of said vessel in a plane, for moving biomass bearing material within said vessel from said first end to said second end of said reaction vessel, and from said second end to said first end of said reaction vessel, said auger vanes having a base edge attached to an interior vessel wall, and a top edge, said top edge of said auger vanes defining a bore oriented parallel to an axis of the reaction vessel, said top edge further including a plurality of paddles extending into said bore in the same plane as said auger vane; and
   a plurality of sparging lines operably connected to an interior of said vessel for injecting steam into said vessel.

2. The biomass bearing material treatment pressure vessel of claim 1 in which said cylindrical reaction vessel is configured for adjustability of the angle from horizontal.

3. The biomass bearing material treatment pressure vessel of claim 1 in which said cylindrical reaction vessel is configured for rotation at an angle of approximately 3-15 degrees from horizontal.

4. The biomass bearing material treatment pressure vessel of claim 1 in which said cylindrical reaction vessel is configured at an angle of approximately 4-8 degrees from horizontal.

5. The biomass bearing material treatment pressure vessel of claim 4 in which said cylindrical reaction vessel includes a single access door.

6. The biomass bearing material treatment pressure vessel of claim 1 in which said cylindrical reaction vessel is configured at an angle of approximately 6 degrees from horizontal.

7. The biomass bearing material treatment pressure vessel of claim 1, which further includes a rotary manifold operably connected to the sparging lines for injecting steam into said sparging lines while said vessel is rotating.

8. The biomass bearing material treatment pressure vessel of claim 1 which further includes an effluents condensation system operably connected to the reaction vessel comprising a steam eductor and a barometric condensing chamber.

9. The biomass bearing material treatment pressure vessel of claim 1 which further includes a swing away door assembly adjacent said access opening, with said door assembly comprising:
a swing away door;
a davit assembly for supporting said swing away door, said davit assembly comprising a generally vertical davit upright, which supports and is rotatably connected to a generally horizontal door support arm, said support arm having a first end and a second end, said first end having a counterweight, and said second end being attached to said door; wherein
said davit assembly is configured to rotate about said davit upright, so that said door may be rotated away from or toward said access opening.

10. The biomass bearing material treatment pressure vessel of claim 1 which further includes one or more chain sections attached to said vessel, so that when said vessel rotates, said one or more chains agitate and shred said biomass bearing material.

11. The biomass bearing material treatment pressure vessel of claim 1 which is configured to rotate in one direction to load and pulverize biomass bearing material and is reversible to rotate in an opposite direction to unload and further shred said biomass bearing material.

12. The biomass bearing material treatment pressure vessel of claim 1 in which said door sealing system comprises a first locking rim surrounding said access opening on the reactor vessel; a second locking rim on said door for placement adjacent the first locking rim, and a clamp collar for sealing the locking rims together and holding said door over the access opening.

13. The biomass bearing material treatment pressure vessel of claim 12, in which said clamp collar further comprises a first section and a second section, and one or more joining devices for joining the first section with the second section.

14. The biomass bearing material treatment pressure vessel of claim 13, in which the joining device is one or more clamp screws which draw the first and second sections together, and hold them together until released.

15. The biomass bearing material treatment pressure vessel of claim 14, which further comprises two clamp screws, which draw the first and second sections together at the ends of each section.

16. The biomass bearing material treatment pressure vessel of claim 15, in which the two clamp screws are driven by one or more motors to open and close said clamp collar by moving said first and second sections of said clamp collar towards or away from each other.

17. The biomass bearing material treatment pressure vessel of claim 1 wherein said bore has a diameter measuring approximately one third of the diameter of the reaction vessel at a corresponding point.

18. A biomass bearing material treatment pressure vessel, comprising:

a generally cylindrical reaction vessel having first and second ends, said reaction vessel configured for rotation and held at an angle of approximately 6% from horizontal;
a drive mechanism for causing rotation of the reaction vessel;
one or more support tracks and wheels to support said reaction vessel as it rotates;
a single access opening in said reaction vessel, through which biomass bearing material may pass;
a door for closing said access opening;
a door sealing system operatively associated with said door for sealing said door to said vessel at said access opening and for maintaining a pressure differential between the interior of said vessel and an exterior thereof;
at least one flight of auger vanes on an interior wall of said reaction vessel and extending into the interior of said vessel in a plane, for moving biomass bearing material within said vessel from said first end to said second end of said reaction vessel, and from said second end to said first end of said reaction vessel, said auger vanes having a base edge attached to an interior vessel wall, and a top edge, said top edge of said auger vanes defining a bore oriented parallel to an axis of the reaction vessel, said top edge further including a plurality of paddles extending into said bore in the same plane as said auger vane; and
a plurality of sparging lines operably connected to an interior of said vessel for injecting steam into said vessel.

19. The biomass bearing material treatment pressure vessel of claim 18 in which said paddles are generally rectangular in shape and attached to said auger vanes with support posts.

20. The biomass bearing material treatment pressure vessel of claim 18 in which said paddles are spaced apart from said auger vane.

21. The biomass bearing material treatment pressure vessel of claim 18 wherein said bore has a diameter measuring approximately one third of the diameter of the reaction vessel at a corresponding point.

22. A biomass bearing material treatment pressure vessel, comprising:
a generally cylindrical reaction vessel with a first end and a second end, with said reaction vessel configured for rotation at an angle selected by the operator;
a drive mechanism for causing rotation of the reaction vessel;
an access opening in said reaction vessel, through which product may enter and/or exit said reaction vessel;
one or more flights of auger vanes on the interior wall of said reaction vessel, for moving product in said reaction vessel, with the auger vanes having a base edge attached to a interior vessel wall, and a top edge, wherein said top edge further includes a plurality of paddles extending into said bore in the same plane as said auger vane;
a plurality of sparging lines operably connected to an interior of the reaction vessel for injecting steam into the interior of the vessel;
a self aligning door sealing assembly, comprising:
a swing away door;
a first locking rim surrounding said access opening on the reactor vessel;
a second locking rim on said door for placement adjacent the first locking rim; and
a clamp collar for drawing said locking rims together and for forming a seal between said door and said access opening for maintaining a pressure differential between the interior of said vessel and an exterior thereof and producing a seal facilitating a buildup of pressure inside the reaction vessel.

23. The biomass bearing material treatment pressure vessel of claim 22, which further comprises a davit assembly for supporting said swing away door, said davit assembly comprising a generally vertical davit upright, which supports and is rotatably connected to a generally horizontal door support arm, said support arm having a first end and a second end, said first end having a counterweight, and said second end being attached to said access opening door;

wherein said davit assembly is configured to rotate about said davit upright, so that said access opening door may be rotated away from or toward said access opening, and when adjacent said access opening, said door sealing system can seal said door to said access opening.

24. The biomass bearing material treatment pressure vessel of claim 23, in which said davit is configured to remain attached to the door as the door is opened and closed, and moved away from the reaction vessel.

25. The biomass bearing material treatment pressure vessel of claim 22, in which said clamp collar further comprises a first section and a second section, and one or more joining devices for joining the first section with the second section.

26. The biomass bearing material treatment pressure vessel of claim 22, in which the joining device is one or more clamp screws which draw the first and second sections together, and hold them together until released.

27. The biomass bearing material treatment pressure vessel of claim 26, in which said joining device further comprises two clamp screws, which draw the first and second sections together at the ends of each section.

28. The biomass bearing material treatment pressure vessel of claim 27, in which said two clamp screws are driven by one or more motors to open and close said clamp collar by moving said first and second sections of said clamp collar toward or away from each other.

29. The biomass bearing material treatment pressure vessel of claim 22, in which said first locking rim and said second locking rim each further comprise a bevel edge on a side opposite a contact side of each, and said clamp collar comprises two matching bevel surfaces which guide and force said locking rims into alignment and pressure tight engagement.

* * * * *